(12) United States Patent
Weber et al.

(10) Patent No.: US 8,163,744 B2
(45) Date of Patent: Apr. 24, 2012

(54) TETRAHYDRO-ISOQUINOLIN-1-ONES FOR THE TREATMENT OF CANCER

(75) Inventors: Lutz Weber, Germering (DE); Vladimir Khazak, Brooklyn, NY (US); Günther F Ross, München (DE); Cotïc Kalinski, München (DE); Christoph Burdack, München (DE)

(73) Assignee: NexusPharma, Inc., Langhorne, PA (US)

( * ) Notice: Subject to any disclaimer, the term of this patent is extended or adjusted under 35 U.S.C. 154(b) by 923 days.

(21) Appl. No.: 11/909,014

(22) PCT Filed: Mar. 17, 2006

(86) PCT No.: PCT/EP2006/002471
§ 371 (c)(1),
(2), (4) Date: Jun. 23, 2008

(87) PCT Pub. No.: WO2006/097323
PCT Pub. Date: Sep. 21, 2006

(65) Prior Publication Data
US 2009/0068144 A1    Mar. 12, 2009

(30) Foreign Application Priority Data

Mar. 18, 2005 (DE) .......................... 10 2005 012 680

(51) Int. Cl.
*C07D 413/02* (2006.01)
*A61K 31/47* (2006.01)

(52) U.S. Cl. ................ 514/235.2; 514/253.05; 514/309; 544/128; 544/363; 546/141

(58) Field of Classification Search .......................... None
See application file for complete search history.

(56) References Cited

U.S. PATENT DOCUMENTS

2005/0049240 A1 *   3/2005   Gribenow et al. ....... 514/217.07

FOREIGN PATENT DOCUMENTS

JP         2003313168 A  *  11/2003
WO         03/095625 A2     11/2003

OTHER PUBLICATIONS

Kandinska et al, Farmatsiya (Sofia, Bulgaria) (2005), 52(1-2), 16-23.*
Boyd et al, Journal of the Chemical Society, Perkin Transactions 1, Organic and Bio-Organic Chemistry (1972-1999), 1978.*
West, Anthony R., Solid State Chemistry and its Applications, Wiley, New York, 1988, pp. 358 & 365.*
Wu et al., Toxicology, 236, pp. 1-6, 2007.*
Vanessa Bres et al., "A non-proteolytic role for ubiquitin in Tat-mediated transactivation of the HIV-1 promoter", Nature Cell Biology, 5(8): 754-761 and attached figures S1-S4 and figure legends (pp. 24-25) (2003).

Matthew J. Fisher et al., "Non-Peptide RGD Surrogates Whcih Mimic a Gly-Asp B-Turn: Potent Antagonists of Platelet Glycoprotein IIb-IIIa", J. Med. Chem., 40: 2085-2101 (1997).
Peter S. Gelatin et al., "A Nonpeptidic Sulfonamide Inhibits the p53-mdm2 Interaction and Activates p53-Dependent Transcription in mdm2-Overexpressing Cells", J. Med. Chem., 47: 4163-4165 (2004).
Bruce L. Grasberger et al., "Discovery and Cocrystal Structure of Benzodiazepinedione HDM2 Antagonists That Activate p53 in Cells", J. Med. Chem., 48: 909-912 (2005).
Ian R. Hardcastle et al., "Isoindolinone-based in inhibitors of the MDM2-p53 protein-protein interaction", Bioorganic & Medicinal Chemistry Letters, 15: 1515-1520 (2005).
Wilhelm Henning et al., "MDM2 Is a Target of Simian Virus 40 in Cellular Transformation and during Lytic Infection", Journal of Virology, 71(10): 7609-7618 (1997).
Monica Hollstein et al., "p53 Mutations in Human Cancers", Science, 253: 49-53 (1991).
Tamar Juven-Gershon et al., "The Mdm2 Oncoprotein Interacts with the Cell Fate Regulator Numb", Molecular and Cellular Biology, 18(7): 3974-3982 (1998).
Dan Michael et al., "The p53-Mdm2 module and the ubiquitin system", Seminars in Cancer Biology, 13: 49-58 (2003).
Jamil Momand et al., "The MDM2 gene amplification database", Nucleic Acids Research, 26(15): 3453-3459 (1998).
Madeleine G. Moule et al., "Role for PP2A in ARF signaling to p53", PNAS, 101(39): 14063-14066 (2004).
Clodagh C. O'Shea et al., "Modulation of the ARF-p53 Pathway by the Small DNA Tumor Viruses", Cell Cycle, 4(3): 449-452 (2005).
Daniel J. Parks et al., 1,4-Benzodiazepine-2,5-diones as small molecule antagonists of the HDM2-p53 interaction: discovery and SAR, Bioorganic & Medicinal Chemistry Letters, 15: 765-770 (2005).
Lyubomir T. Vasilev et al., "In Vivo Activation of the p53 Pathway by Small-Molecule Antagonists of MDM2", Sciencexpress, (2004).
Karen H. Vousden et al., "Live or Let Die: The Cell's Response to p53", Nature, 2: 594-604 (2002).

(Continued)

*Primary Examiner* — Zinna Northington Davis
(74) *Attorney, Agent, or Firm* — Patrick J. Hagan; Dann, Dorfman, Herrell and Skillman, P.C.

(57) ABSTRACT

The present invention provides a compound selected from compounds of formula I as ligand binding to the HDM2 protein, inducing apoptosis and inhibiting proliferation, and having therapeutic utility in cancer therapy. Compounds of formula (I) can be used as therapeutics for treating stroke, myocardial infarction, ischemia, multi-organ failure, spinal cord injury, Alzheimer's Disease, injury from ischemic events, heart valvular degenerative disease Moreover, compounds of formula (I) can be used to decrease the side effects from cytotoxic cancer agents and to treat viral infections.

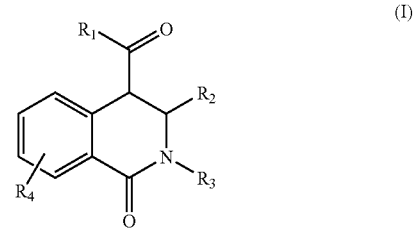

6 Claims, No Drawings

OTHER PUBLICATIONS

Hai Liang Yang, "Adenovirus-mediated E2F-1 Gene Transfer Inhibits MDM2 Expression and Efficiently Induces Apoptosis in MDM2-overexpressing Tumor Cells", Clinical Cancer Research, 5: 2242-2250 (1999).

Zhuo Zhang et al., "MDM2 is a Negative Regulator of p21 WAF1/C1P1, Independent of p53", The Journal of Biological Chemistry, 279(16): 16000-16006 (2004).

Zhuo Zhang et al., "Antisense therapy targeting MDM2 oncogene in prostate cancer: Effects on proliferation, apoptosis, multiple gene expression, and chemotherapy", PNAS, 100(20): 11636-11641 2003).

Jianhua Zhao et al., "The initial evaluation of non-peptidic small-molecule HDM2 inhibitors based on p53-HDM2 complex structure", Cancer Letters, 183: 69-77 (2002).

Keigo Machida et al., "Hepatitis C virus induces a mutator phenotype: Enhanced mutations of immunoglobulin and protooncogenes", PNAS, 101(12) 4262-4267 (2004).

* cited by examiner

TETRAHYDRO-ISOQUINOLIN-1-ONES FOR THE TREATMENT OF CANCER

CROSS-REFERENCE TO RELATED APPLICATIONS

This application is the U.S. National Stage of International Application No. PCT/EP2006/002471, filed 17 Mar. 2006, the entire disclosure of which is incorporated by reference in their entireties in the present application.

BACKGROUND OF THE INVENTION

HDM2 plays a central role in regulating and influencing important cell-signalling pathways. HDM2 is known to interact with a range of different proteins that influence cellular apoptosis, proliferation and survival.

Thus, amongst other proteins, HDM2 binds to the tumor suppressor protein p53 and targets this protein for ubiquitination and degradation, prevents translocation of p53 to the nucleus by facilitating translocation to the microsomes. Thereby, HDM2 prevents transactivation of p53 target genes that are implicated in the regulation of cell cycle and apoptosis. The p53 protein is a potent cell cycle inhibitor that prevents propagation of permanently damaged cell clones by the induction of growth arrest or apoptosis, resulting in the protection against development of cancer by guarding cellular integrity.

Both p53 as well as HDM2 can be associated with cancer: about 50% of all human tumors harbor a mutation or deletion in the p53 gene that impairs normal p53 function (Hollstein et al. *Science* 1991, 253, 49-53). In many cancers with wild-type p53, HDM2 is overexpressed, disabling the normal p53 function (Momand et al. *Nucleic Acids Res.* 1998, 26, 3453-3459).

The HDM2 gene has a p53-responsive promoter element and elevated levels of p53 that translocate to the nucleus induce expression of HDM2. Induction of HDM2 by p53 forms an autoregulatory feedback loop, ensuring low levels of both HDM2 and p53 in normally proliferating cells (Michael and Oren *Semin. Cancer Biol.* 2003, 13, 49-58; Vousden and Lu *Nature Reviews Cancer* 2002, 2, 594-604). However, in many cancers this normal ratio of HDM2 to p53 is changed and misregulated.

Inhibiting the interaction of HDM2 with p53 in cells with wild-type p53 or mutated p53 should lead to an increase of p53 levels in the cytosole, facilitating normal nuclear translocation of normal or mutated p53, cell cycle arrest and/or apoptosis and restoring the tumor suppressor role of p53. The feasibility of this strategy has been shown by the use of different macromolecular tools for inhibition of HDM2-p53 interaction (e.g. antibodies, antisense oligonucleotides, peptides).

HDM2 also binds to the tumor suppressor pRB, as well as E2F-1 (Yang et al. *Clinical Cancer Research* 1999, 5, 2242-2250).

E2F-1 is a transcription factor that regulates S phase entry and has been shown to cause apoptosis in some cell types when overexpressed. HDM2 binds to E2F through a conserved binding region at p53, activating E2F-dependent transcription of cyclin A, and suggesting that HDM2 small molecule ligands or antagonists might have also anti-tumor effects in cells independent of their role of restoring p53 function.

HDM2 can associate in vitro and in vivo with the mammalian Numb protein. The association occurs through the N-terminal domain of HDM2, which is the region also involved in p53 binding. The Numb protein is involved in the regulation of cell fate and in a variety of developmental processes, most notably in the nervous system. Through its interaction with Numb, HDM2 may influence processes such as differentiation and survival. This could also contribute to the altered properties of tumor cells, which overexpress HDM2 (Juven-Gershon et al. *Mol. Cell. Biol.* 1998, 18, 3974-3982).

There is also evidence that HDM2 has a direct role in the regulation of p21, a cyclin-dependent kinase inhibitor. The inhibition of HDM2 with anti-HDM2 antisense oligonucleotide or Short Interference RNA targeting HDM2 significantly elevates p21 protein levels in p53 null PC3 cells. In contrast, overexpression of HDM2 diminishes p21 levels by shortening the p21 half-life, an effect reversed by HDM2 antisense inhibition. HDM2 facilitates p21 degradation independent of ubiquitination and the E3 ligase function of HDM2. Instead, HDM2 promotes p21 degradation by facilitating binding of p21 with the proteasomal C8 subunit. The p21 and HDM2 bind through 180—the 298 amino acids region of the HDM2 protein (Zhang et al. *J. Biol. Chem.* 2004, 279, 16000-16006).

There is also evidence for a malfunctioning HDM2 regulation having effect on a proper p53 function and causing cancer, beyond mutated p53 or overexpression of HDM2. Thus, when E2F signals the growth of a cancer, P14ARF is dispatched to break down HDM2, freeing p53 to kill the cancer cell. In certain cancers P14ARF is lacking (Moule et al. *Proc. Natl. Acad. Sci. U.S.A.* 2004, 101, 14063-6). P14ARF binds to HDM2 and promotes the rapid degradation of HDM2. ARF-mediated HDM2 degradation is associated with HDM2 modification and concurrent p53 stabilization and accumulation.

The validity of inhibiting HDM2 as a therapeutic concept has been first demonstrated by antisense HDM2 inhibitors that exhibit significant antitumor activity in multiple human cancer models with various p53 statuses (Zhang et al. *Proc. Natl. Acad. Sci. U.S.A.* 2003, 100, 11636-11641).

Small molecule antagonists of the HDM2 protein interactions may therefore offer a viable approach towards cancer therapy, either as single agents or in combination with a broad variety of other anti-tumor therapies.

There is also growing evidence that HDM2 plays an important role in viral infections. First, it is known that viruses rely on changing normal p53 signalling (O'shea and Fried M. *Cell Cycle* 2005; Machida et al. *Proc. Natl. Acad. Sci. U.S.A.* 2004, 23, 101, 4262-7).

Second, HDM2 directly interacts with viral proteins, for example HDM2 is a target of simian virus 40 in cellular transformation and during lytic infection (Henning et al. *J. Virol.* 1997, 71, 7609-7618). Furthermore, the HDM2 protein, like p53, becomes metabolically stabilized in SV40-transformed cells. This suggests the possibility that the specific targeting of HDM2 by SV40 is aimed at preventing HDM2-directed proteasomal degradation of p53 in SV40-infected and -transformed cells, thereby leading to metabolic stabilization of p53 in these cells. A trimeric LT-p53-HDM2 complex is formed with simian virus 40 large tumor antigen (LT) in SV40-transformed cells.

The human immunodeficiency virus type 1 (HIV-1) encodes a potent transactivator, Tat. HDM2 has been shown to interact with Tat and mediating its ubiquitination in vitro and in vivo. In addition, HDM2 is a positive regulator of Tat-mediated transactivation, indicating that the transcriptional properties of Tat are stimulated by ubiquitination (Bres et al. *Nat Cell Biol.* 2003, 5, 754-61).

Small molecule inhibitors of the HDM2 interaction have been reported and show pro-apoptotic effects in in vitro models and an antitumor effect in animal models of cancer. Thus, benzodiazepines have been used as a chemical scaffold to achieve HDM2 inhibitory activity (Grasberger et al. *J. Med. Chem.* 2005, 48, 909-912; Parks et al. *Bioorganic & Medicinal Chemistry Letters* 2005, 15, 765-770). Similarly, imidazolines (Vassilev et al. *Science* 2004, 303, 844-848), isoindolones (Hardcastle et al. *Bioorganic & Medicinal Chemistry Letters* 2005, 15, 1515-1520), norbornanes (Zhao et al. *Cancer Letters* 2002, 183, 69-77) and sulfonamides (Galatin and Abraham *J. Med. Chem.* 2004, 47, 4163-4165) have been reported as small molecule HDM2 inhibitors.

It has also been reported that HDM2 ligands have a cytoprotective effect. Thus, HDM2 inhibitors can be employed in methods of inducing cytoprotection and are useful to protect non-target cells against the harmful effects of chemotherapeutic agents. The amount of HDM2 inhibitor that provides such an effect can be about 5 to about 10 fold lower than the amount needed to induce apoptosis (Koblish et al. WO03095625, METHOD FOR CYTOPROTECTION THROUGH HDM2 AND HDM2 INHIBITION, 2003-11-20).

Isoquinolones have been reported already as potent antagonists of the platelet glycoprotein IIb-IIIa (Fisher et al. *J. Med. Chem.* 1997, 40, 2085-2101) to treat cardiovascular diseases.

Pancrastatin is a naturally occurring alkaloid with an isoquinolone structure exhibiting anticancer properties, by acting on the tubulin cytosceleton. Lysolipin and Cervinomycin are antibiotics isolated from *streptomyces violaceoniger*. Lycoricidine and narciclasine are isoquinolone based plant-growth regulators, Gliquidone is an antidiabetic medication which is used in those patients with adult maturity onset or non-insulin dependent diabetes (NIDDM). It works by lowering blood sugar levels by stimulating the production and release of insulin from the pancreas. It also promotes the movement of sugar from the blood into the cells in the body which need it. Tesicam is an isoquinolon-dione used for its anti-inflammatory properties. These compounds have low toxicity, good pharmaco-kinetic properties and render the chemical class of isoquinolones an interesting scaffold for new drug candidates.

In this present invention, we describe novel, isoquinolone scaffold based small molecules that are inhibitors of HDM2 and can be used as novel therapeutic agents.

SUMMARY OF THE INVENTION

The present invention provides compounds of formula I and the pharmaceutically acceptable salts and esters thereof, which are ligands binding to the HDM2 protein, inducing apoptosis and inhibiting proliferation, and having therapeutic utility in cancer therapy. This therapeutic effect can be achieved by using compounds of formula I alone or in combination with other agents that are used to treat cancer.

Second, compounds of formula I also can be used to treat cancer by protecting non-cancer cells from the deleterious effects of cancer treating drugs. In this treatment, a combination of an antineoplastic agent and a cytoprotective amount of at least one compound of formula I, and one or more pharmaceutically acceptable excipients are used. The compound of formula I, also called a HDM2 ligand is administered prior to, concurrently or after administration of the antineoplastic agent. Additionally, the HDM2 inhibitor can be administered continuously or at repeated regular intervals.

Third, a compound of formula I can be used as a therapeutic agent in methods of treating stroke, myocardial infarction, ischemia, multi-organ failure, spinal cord injury, Alzheimer's Disease, injury from ischemic events, heart valvular degenerative disease or decreasing the side effects from cytotoxic agents, such as hair loss or cardio toxicity induced by doxorubicin.

Fourth, a compound of formula I of the present invention can be used to treat viral infections, especially in a pharmaceutical composition comprising a known antiviral compound.

Fifth, a compound of formula I of the present invention is directed to a pharmaceutical composition comprising a cytoprotective amount of an HDM2 ligand, and one or more pharmaceutically acceptable excipients.

DETAILED DESCRIPTION OF THE INVENTION

The present invention provides isoquinolinone derivatives that are small molecule ligands of the HDM2 protein and prevent binding of other proteins to HDM2.

In in vitro cell-free and cell-based assays, compounds of the present invention inhibit the interaction of the HDM2 protein with a p53-derived peptide. In cell-based assays, these compounds demonstrate mechanistic activity such as induction of apoptosis and inhibition of proliferation. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of HDM2 antagonists is likely linked to its mechanism of action. These compounds can be potent and selective anticancer agents.

The present invention provides a compound of formula I and pharmaceutically acceptable esters and salts thereof,

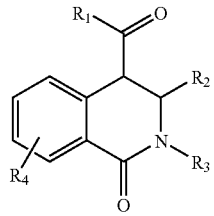

formula I wherein R1 is selected from substituted or unsubstituted morpholinyl, substituted or unsubstituted pyrrolidinyl and substituted or unsubstituted piperazinyl, —O(X1) or —NX1(X2), with X1 and X2 independently selected from H, alkyl, cycloalkyl, heteroalkyl, aryl, heteroaryl, arylalkyl or heteroarylalkyl, wherein R2 and R3 are independently selected from aryl, heteroaryl, arylalkyl or heteroarylalkyl, wherein R4 is selected from —H, —F, —Cl, —Br, —I, —NO2, hydroxy, lower alkyl, lower alkenyl or lower alkinyl, lower alkoxy, such as —OCH3, —CH2OCH3 and —CH2OCH2CH3, —NY1(Y2), with Y1 and Y2 independently selected from H, lower alkyl, lower alkoxy alkyl, hetero alkyl, aryl or heteroaryl.

A preferred embodiment of the present invention relates to compounds of formula I, wherein
R1 is selected from substituted or unsubstituted morpholinyl, substituted or unsubstituted pyrrolidinyl and substituted or unsubstituted piperazinyl, —O(X1) or —NX1(X2), with X1 and X2 independently selected from H, alkyl, cycloalkyl, heteroalkyl, aryl, heteroaryl, arylalkyl or heteroarylalkyl, and R2 and R3 are each independently selected from aryl, heteroaryl, 1H-indol-3-yl, naphthal-2-yl, quinolin-3-yl, phenyl, substituted phenyl, 3- or 4-fluorophenyl, 3- or 4-chlorophenyl, 3- or 4-bromophenyl, 3- or 4-iodophenyl, benzyl, substituted benzyl, 3- or 4-fluorobenzyl, 3- or 4-chlorobenzyl, 3- or 4-bromobenzyl, 3- or 4-iodobenzyl and R4 is selected from —H, —F, —Cl, —Br, —I, —NO2, hydroxy, lower alkyl, lower alkenyl or lower alkinyl, lower alkoxy, such as —OCH3, —CH2OCH3 and —CH2OCH2CH3, —NY1(Y2), with Y1 and Y2 independently selected from H, lower alkyl, lower alkoxy alkyl, hetero alkyl, aryl or heteroaryl.

A further preferred embodiment of the present invention relates to compounds of formula I, wherein
R2 is selected from phenyl, substituted phenyl, 1H-indol-3-yl, naphthal-2-yl, quinolin-3-yl, 3- or 4-fluorophenyl, 3- or 4-chlorophenyl, 3- or 4-bromophenyl, 3- or 4-iodophenyl and R3 is selected from benzyl, substituted benzyl, 1H-indol-3-methyl, naphthal-2-yl, quinolin-3-yl, 3- or 4-fluorobenzyl, 3- or 4-chlorobenzyl, 3- or 4-bromobenzyl, 3- or 4-iodobenzyl.

A further preferred embodiment of the present invention relates to compounds of formula I, wherein
R2 is selected from benzyl, substituted benzyl, 1H-indol-3-methyl, naphthal-2-yl, quinolin-3-yl, 3- or 4-fluorobenzyl, 3- or 4-chlorobenzyl, 3- or 4-bromobenzyl, 3- or 4-iodobenzyl and R3 is selected from phenyl, substituted phenyl, 1H-indol-3-yl, naphthal-2-yl, quinolin-3-yl, 3- or 4-fluorophenyl, 3- or 4-chlorophenyl, 3- or 4-bromophenyl, 3- or 4-iodophenyl.

A further preferred embodiment of the present invention relates to compounds of formula I, wherein
R1 is selected from dimethylaminyl, diethylaminyl, morpholinyl, piperazinyl, N-methyl-piperazinyl, N-acetyl-piperazinyl, N-2-hydroxyethyl-piperazinyl, 2-oxo-N-alkyl-piperazinyl, 2-oxo-N-heteroalkyl-piperazinyl, pyrrolidinyl, 2-oxo-pyrrolidinyl or 2-carboxy-pyrrolidinyl.

A further preferred embodiment of the present invention relates to compounds of formula I, wherein
R1 is selected from —OX1 or —NH(X2), wherein X1 is selected from —H or lower alkyl, and X2 is selected from H, —CH2CH2OH, —CH2CH2OCH3, lower alkyl, lower heteroalkyl, cycloalkyl, heteroalkyl, aryl, heteroaryl, arylalkyl or heteroarylalkyl.

A further preferred embodiment of the present invention relates to compounds of formula I, wherein
R1 is selected from —OX1 or —NH(X2), wherein X1 is selected from —H or lower alkyl, and X2 is selected from H, —CH2CH2OH, —CH2CH2OCH3, lower alkyl, lower heteroalkyl, cycloalkyl, heteroalkyl, aryl, heteroaryl, arylalkyl or heteroarylalkyl and R2 is selected from phenyl, substituted phenyl, 1H-indol-3-yl, naphthal-2-yl, quinolin-3-yl, 3- or 4-fluorophenyl, 3- or 4-chlorophenyl, 3- or 4-bromophenyl, 3- or 4-iodophenyl and R3 is selected from benzyl, substituted benzyl, 1H-indol-3-methyl, naphthal-2-yl, quinolin-3-yl, 3- or 4-fluorobenzyl, 3- or 4-chlorobenzyl, 3- or 4-bromobenzyl, 3- or 4-iodobenzyl and R4 is selected from —H, —F, —Cl, —Br, —I, —NO2, hydroxy, lower alkenyl or lower alkinyl, lower alkoxy, such as —OCH3, —CH2OCH3 and —CH2OCH2CH3, —NY1(Y2), with Y1 and Y2 independently selected from H, lower alkyl, lower alkoxy alkyl, hetero alkyl, aryl or heteroaryl.

A further preferred embodiment of the present invention relates to compounds of formula I, wherein
R1 is selected from —OX1 or —NH(X2), wherein X1 is selected from —H or lower alkyl, and X2 is selected from H, —CH2CH2OH, —CH2CH2OCH3, lower alkyl, lower heteroalkyl, cycloalkyl, heteroalkyl, aryl, heteroarylalkyl, aryl or heteroarylalkyl and R2 is selected from benzyl, substituted benzyl, 1H-indol-3-methyl, naphthal-2-yl, quinolin-3-yl, 3- or 4-fluorobenzyl, 3- or 4-chlorobenzyl, 3- or 4-bromobenzyl, 3- or 4-iodobenzyl and R3 is selected from phenyl, substituted phenyl, 1H-indol-3-yl, naphthal-2-yl, quinolin-3-yl, 3- or 4-fluorophenyl, 3- or 4-chlorophenyl, 3- or 4-bromophenyl, 3- or 4-iodophenyl and R4 is selected from —H, —F, —Cl, —Br, —I, —NO2, hydroxy, lower alkyl, lower alkenyl or lower alkinyl, lower alkoxy, such as —OCH3, —CH2OCH3 and —CH2OCH2CH3, —NY1(Y2), with Y1 and Y2 independently selected from H, lower alkyl, lower alkoxy alkyl, hetero alkyl, aryl or heteroaryl.

A further preferred embodiment of the present invention relates to compounds selected from the group of: 2-(4-Chloro-benzyl)-3-(4-chloro-phenyl)-1-oxo-1,2,3,4-tetrahydro-isoquinoline-4-carboxylic acid (2-methoxyethyl)-amide; 2,3-Bis-(4-chloro-phenyl)-1-oxo-1,2,3,4-tetrahydro-isoquinoline-4-carboxylic acid (2-methoxyethyl)-amide; 3-(4-Chloro-benzyl)-2-(4-chloro-phenyl)-1-oxo-1,2,3,4-tetrahydro-isoquinoline-4-carboxylic acid (2-methoxyethyl)-amide; 2-(4-Chloro-benzyl)-3-(1H-indol-3-yl)-1-oxo-1,2,3,4-tetrahydro-isoquinoline-4-carboxylic acid (2-methoxyethyl)-amide; (4-Chloro-phenyl)-[3-(4-chloro-phenyl)-4-(2-methoxy-ethylcarbamoyl)-1-oxo-3,4-dihydro-1H-isoquinolin-2-yl]-acetic acid; 2-(4-Chloro-benzyl)-1-oxo-3-quinolin-3-yl-1,2,3,4-tetrahydro-isoquinoline-4-carboxylic acid (2-methoxyethyl)-amide; 2-(4-Chloro-benzyl)-3-naphthalen-2-yl-1-oxo-1,2,3,4-tetrahydro-isoquinoline-4-carboxylic acid (2-methoxyethyl)-amide; 2-(4-Chloro-benzyl)-3-(4-chloro-phenyl)-1-oxo-1,2,3,4-tetrahydro-isoquinoline-4-carboxylic acid; 2,3-Bis-(4-chloro-phenyl)-1-oxo-1,2,3,4-tetrahydro-isoquinoline-4-carboxylic acid; 3-(4-Chloro-benzyl)-2-(4-chloro-phenyl)-1-oxo-1,2,3,4-tetrahydro-isoquinoline-4-carboxylic acid; 2-(4-Chloro-benzyl)-3-(1H-indol-3-yl)-1-oxo-1,2,3,4-tetrahydro-isoquinoline-4-carboxylic acid; 2-[Carboxy-(4-chloro-phenyl)-methyl]-3-(4-chloro-phenyl)-1-oxo-1,2,3,4-tetrahydro-isoquinoline-4-carboxylic acid; 2-(4-Chloro-benzyl)-1-oxo-3-quinolin-3-yl-1,2,3,4-tetrahydro-isoquinoline-4-carboxylic acid; 2-(4-Chloro-benzyl)-3-(4-chloro-phenyl)-4-(morpholine-4-carbonyl)-3,4-dihydro-2H-isoquinolin-1-one; 4-(4-Acetyl-piperazine-1-carbonyl)-2-(4-chloro-benzyl)-3-(4-chloro-phenyl)-3,4-dihydro-2H-isoquinolin-1-one; 4-(4-Acetyl-piperazine-1-carbonyl)-2-(4-chloro-benzyl)-3-(4-chloro-phenyl)-3,4-dihydro-2H-isoquinolin-1-one; 2-(4-Chloro-benzyl)-3-(4-chloro-phenyl)-1-oxo-1,2,3,4-tetrahydro-isoquinoline-4-carboxylic acid (2-hydroxy-ethyl)-amide; 2-(4-Chloro-benzyl)-3-(4-chloro-phenyl)-4-[4-(2-hydroxy-ethyl)-piperazine-1-carbonyl]-3,4-dihydro-2H-isoquinolin-1-one.

The present invention further provides pharmaceutical compositions comprising a compound of formula I as defined herein or a pharmaceutically acceptable ester, prodrug, hydrate, solvate or salt thereof, optionally in combination with a pharmaceutically acceptable carrier.

A further preferred embodiment of the present invention relates to pharmaceutical compositions comprising a compound of formula I as defined herein or a pharmaceutically acceptable ester, prodrug, hydrate, solvate or salt thereof, optionally in combination with a pharmaceutically acceptable carrier, further comprising one or more other anti-tumor agents.

A further preferred embodiment of the present invention relates to pharmaceutical compositions comprising a compound of formula I as defined herein or a pharmaceutically acceptable ester, prodrug, hydrate, solvate or salt thereof, optionally in combination with a pharmaceutically acceptable carrier, further comprising one or more other anti-tumor agents, wherein the anti-tumor agent is selected from 16-Aza-epothilone B, Aldesleukin, Amifostine, Aranose, Bevacizumab, Bleocin, Bleomycin, BMS-184476, Bortezomib, Calcitriol, Carmustine, Canertinib, Canfosfamide, Capecitabine, Carboplatin, Carmustine, Cefixime, Ceftriaxone, Celecoxib, Celmoleukin, Cetuximab, Ciclosporin, Cisplatin, Clodronate, Cyclophosphamide, Cytarabine, Deoxorubicin, Desoxyepothilone B, Diethylstilbestrol, Diflomotecan, Docetaxel, Doxorubicin, Edatrexate, Efaproxiral, EKB-569, Epirubicin, Epratuzumab, Erlotinib, Etoposide, Exatecan, Fludarabine, Fluorouracil, Folinic acid, Galarubicin, Gefinitib, Gemcitabine, Gemtuzumab, Gimatecan, Glufosfamide, Granisetron, Homoharringtonine, Hyaluronic acid, Ibandronate, Ibritumomab, Ifosfamide, Imatinib, Interferon alfa, Interferon alfa-2a, Interferon alfa-2b, Irinotecan, Isoflavone, Isotretinoin, Ixabepilone, Ketoconazole, Lapatinib, Leflunomide, Lenograstim, Leucovorin, Lexidronam, Linezolid, Lometrexol, Lurtotecan, MEN-10755, Methotrexate, Mitomycin, Neridronate, Nimesulide, Nitroglycerin, O6-Benzylguanine, Omeprazole, Ortataxel, Oxaliplatin, Paclitaxel, Patupilone, Pegfilgrastim, PEG-filgrastim, Pelitinib, Pemetrexed, Pentostatin, Perifosine, Plevitrexed, Polyprenoic acid, Quinupristin, Raloxifene, Raltitrexed, Ramosetron, Retinoic acid, Risedroante, Rituximab, Rofecoxib, Rubitecan, S-9788, Sabarubicin, Sargramostim, Satraplatin, SN-38, Sorafenib, Suberanilohydroxamic acid, Tamoxifen, Taxotere, Tazarotene, Tegafur, Temozolamide, Tesmilifene, Tetrodotoxin, Thalidomide, Tipifarnib, Topotecan, Trabectedin, Trastuzumab, Traszutumab, Tretinoin, Vatalanib, Vincristine, Vinorelbine, Vinscristine, ZD-6474, Zoledronate or Zosuquidar.

A further preferred embodiment of the present invention relates to pharmaceutical compositions comprising a compound of formula I as defined herein or a pharmaceutically acceptable ester, prodrug, hydrate, solvate or salt thereof, optionally in combination with a pharmaceutically acceptable carrier, further comprising one or more antiviral agents.

A further preferred embodiment of the present invention relates to pharmaceutical compositions comprising a compound of formula I as defined herein or a pharmaceutically acceptable ester, prodrug, hydrate, solvate or salt thereof, optionally in combination with a pharmaceutically acceptable carrier, further comprising one or more antiviral agents, wherein the antiviral agent is selected from 3TC, Abacavir, Adefovir dipivoxil, Acyclovir, Amprenavir, Amantadine, Amoxovir, AZT, Clevudine, Delavirdine, d4T, Emtricitabine, Entecavir, Famciclovir, Ganciclovir, Indinavir, Lamivudine, Nelfinavir, Nevirapine, Oseltamavir, Rimantadine, Ritonavir, Saquinavir, Septrin, Telbivudine, Tenofovir, Valacyclovir, Valtorcitabine, Valopicitabine or Zanamivir.

It is a further object of the present invention to provide for the use of a compound of formula I as defined herein or a pharmaceutical composition as defined herein for the preparation of a medicament for the treatment of cancer.

The term alkyl denotes a saturated or unsaturated (i.e. alkenyl and alkinyl) straight or branched chain alkyl group, containing preferably from one to ten, more preferably one to six carbon atoms for example methyl, ethyl, propyl, iso-propyl, butyl, iso-butyl, sec-butyl, tert-butyl, n-pentyl, iso-pentyl, n-hexyl, 2,2-dimethylbutyl, n-octyl; ethenyl (vinyl), propenyl (allyl), iso-propenyl, n-pentyl, butenyl, isoprenyl or hexa-2-enyl; ethinyl, propinyl or butinyl groups. Any alkyl group as defined herein may be substituted with one, two or more substituents, for example F, Cl, Br, I, NH2, OH, SH, COOH or NO2.

The terms alkenyl and alkinyl denote an unsaturated straight or branched chain alkyl group (having one, two or more double and/or triple bonds, an alkenyl preferably having one or two double bonds and an alkinyl preferably having one or two triple bonds), containing preferably from two to ten, more preferably two to six carbon atoms for example: ethenyl (vinyl), propenyl (allyl), iso-propenyl, n-pentenyl, butenyl, isoprenyl or hexa-2-enyl; ethinyl, propinyl or butinyl groups. Any alkenyl or alkinyl group as defined herein may be substituted with one, two or more substituents, for example F, Cl, Br, I, NH2, OH, SH, COOH or NO2.

The term heteroalkyl denotes an alkyl group as defined herein where one or more carbon atoms are replaced by an oxygen, nitrogen, phosphorous or sulphur atom for example an alkoxy group such as methoxy, ethoxy, propoxy, iso-propoxy, butoxy or tert-butoxy, an alkoxyalkyl group such as methoxymethyl, ethoxymethyl, 1-methoxyethyl, 1-ethoxyethyl, 2-methoxyethyl or 2-ethoxyethyl, an alkylamino group such as methylamino, ethylamino, propylamino, isopropylamino, dimethylamino or diethylamino, an alkylthio group such as methylthio, ethylthio or isopropylthio or a cyano group. It may also refer to one of the above groups containing a keto group. The term heteroalkyl furthermore refers to a group derived from a carboxylic acid or carboxylic acid amide such as acetyl, propionyl, acetyloxy, propionyloxy, acetylamino or propionylamino, a carboxyalkyl group such as carboxymethyl, carboxyethyl or carboxypropyl, a carboxyalkyl ester, an alkylthiocarboxyamino group, an alkoxyimino group, an alkylaminothiocarboxyamino group or an alkoxycarbonylamino group. Any heteroalkyl group as defined herein may be substituted with one, two or more substituents, for example F, Cl, Br, I, NH2, OH, SH, COOH or NO2.

The term cycloalkyl refers to a saturated or partially unsaturated (having one, two or more double and/or triple bonds), cyclic group with one, two or more rings, having preferably three to 14 carbon ring-atoms, more preferably from five or six to ten carbon ring-atoms, for example cyclopropyl, cyclobutyl, cyclopentyl, cyclohexyl, tetralin, cyclopentenyl or cyclohex-2-enyl groups. Any cycloalkyl group as defined herein may be substituted with one, two or more substituents, for example F, Cl, Br, I, OH, NH2, SH, N3, NO2, alkyl groups such as methyl or ethyl, heteroalkyl groups as defined herein, such as methoxy, methylamino, dimethylamino, cyanide, or a group of the formula —OR10, wherein R10 is hydrogen, a group of formula $PO(OR)_2$ or $SO3R$ or a heteroalkyl group carrying at least one OH, NH2, SO3R, $PO(OR)_2$ or COOH group, wherein R is H, alkyl, cycloalkyl, aryl, arylalkyl.

The term aryl refers to an aromatic cyclic group with one, two or more rings, having preferably five to 14 carbon ring-atoms, more preferably from five or six to ten carbon ring-atoms, for example phenyl or naphthyl groups. Any aryl group as defined herein may be substituted with one, two or more substituents, for example F, Cl, Br, I, OH, NH2, SH, N3, NO2, alkyl groups such as methyl or ethyl, heteroalkyl groups such as methoxy, methylamino, dimethylamino or cyanide.

The term heteroaryl refers to an aryl group as defined herein where one, two or more ring-carbon atoms are replaced by an oxygen, nitrogen, boron, phosphorous or sulphur atom, for example pyridyl, imidazolyl, pyrazolyl, quinolinyl, isoquinolinyl, pyrrolyl, oxazolyl, isoxazolyl, thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl and pyridazinyl groups. Any heteroaryl group as defined herein may be substituted with one, two or more substituents, for example F, Cl, Br, I, OH, NH2, SH, N3, NO2, alkyl groups such as methyl or ethyl, heteroalkyl groups such as methoxy, methylamino, dimethylamino or cyanide.

The terms arylalkyl and heteroarylalkyl refer to groups that comprise both aryl or, respectively, heteroaryl as well as alkyl and/or heteroalkyl and/or cycloalkyl groups, each of the groups as defined herein.

The terms lower alkyl, lower alkenyl, lower alkinyl, lower alkoxy, lower alkoxy alkyl and lower heteroalkyl refer to an alkyl group, an alkenyl group, an alkinyl group, an alkoxy group, an alkoxy alkyl group and a heteroalkyl group, respectively, containing one to six carbon atoms, preferably one to four carbon atoms.

Compounds selected from formula I of the present invention are HDM2 ligands and show binding affinities from about 1 nM to about 100 μM to HDM2, preventing binding of p53 and other proteins, inhibition of proliferation and induction of apoptosis in cell based assays.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolongs the survival of the subject being treated, preferably a human. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound being administered, the route of administration, the condition being treated, as well as the patient being treated.

Examples of pharmacologically acceptable salts of sufficiently basic compounds of formula I are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula I may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula I. Compounds of formula I can be solvated, especially hydrated. The hydratization can occur during the process of production or as a consequence of the hygroscopic nature of the initially water free compounds of formula I. The compounds of formula I contain asymmetric C-atoms and may be present either as achiral compounds, mixtures of diastereomers, mixtures of enantiomers or as optically pure compounds.

It should be appreciated that certain compounds of formula (I) may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention.

Examples of different stereoisomers of the present invention are:

(3S,4S)-2-(4-Chloro-benzyl)-3-(4-chloro-phenyl)-1-oxo-1,2,3,4-tetrahydro-isoquinoline-4-carboxylic acid

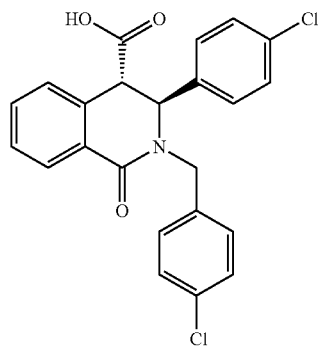

(3S,4R)-2-(4-Chloro-benzyl)-3-(4-chloro-phenyl)-1-oxo-1,2,3,4-tetrahydro-isoquinoline-4-carboxylic acid

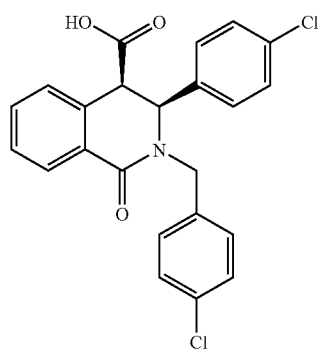

(3R,4R)-2-(4-Chloro-benzyl)-3-(4-chloro-phenyl)-1-oxo-1,2,3,4-tetrahydro-isoquinoline-4-carboxylic acid

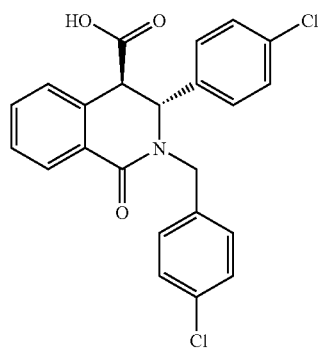

11

(3R,4S)-2-(4-Chloro-benzyl)-3-(4-chloro-phenyl)-1-oxo-1,2,3,4-tetrahydro-isoquinoline-4-carboxylic acid

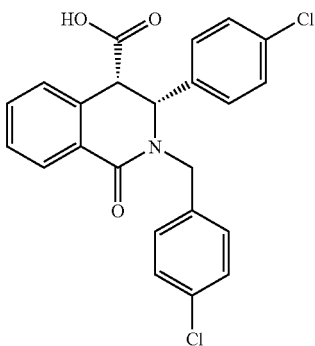

(3S,4S)-2-(4-Chloro-benzyl)-3-(4-chloro-phenyl)-1-oxo-1,2,3,4-tetrahydro-isoquinoline-4-carboxylic acid (2-methoxy-ethyl)-amide

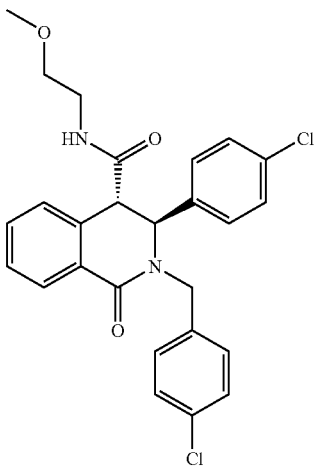

(3S,4R)-2-(4-Chloro-benzyl)-3-(4-chloro-phenyl)-1-oxo-1,2,3,4-tetrahydro-isoquinoline-4-carboxylic acid (2-methoxy-ethyl)-amide

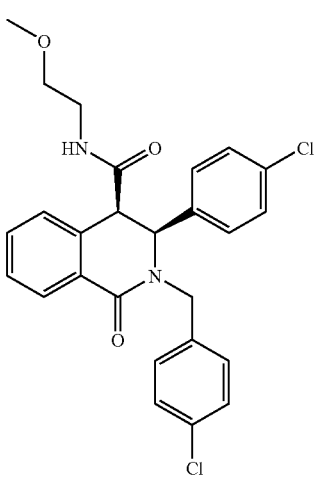

12

(3R,4R)-2-(4-Chloro-benzyl)-3-(4-chloro-phenyl)-1-oxo-1,2,3,4-tetrahydro-isoquinoline-4-carboxylic acid (2-methoxy-ethyl)-amide (3R,4S)-2-(4-Chloro-benzyl)-3-(4-chloro-phenyl)-1-oxo-1,2,3,4-tetrahydro-isoquinoline-4-carboxylic acid (2-methoxy-ethyl)-amide

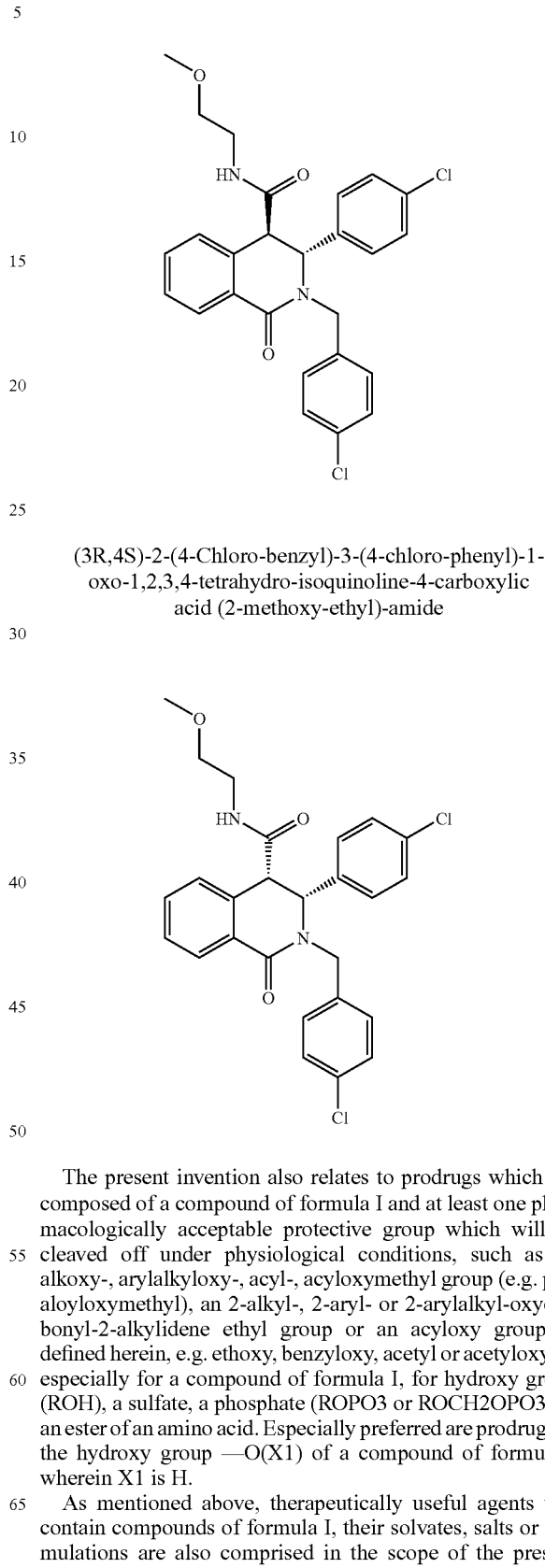

The present invention also relates to prodrugs which are composed of a compound of formula I and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula I, for hydroxy group (ROH), a sulfate, a phosphate (ROPO3 or ROCH2OPO3) or an ester of an amino acid. Especially preferred are prodrugs of the hydroxy group —O(X1) of a compound of formula I wherein X1 is H.

As mentioned above, therapeutically useful agents that contain compounds of formula I, their solvates, salts or formulations are also comprised in the scope of the present invention. In general, compounds of formula I will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups; parenteral including intravenous, intramuscular and subcutaneous injection, e.g. as an injectable solution or suspension; rectal as suppositories; by inhalation or insufflation, e.g. as a powder formulation, as microcrystals or as a spray (e.g. liquid aerosol); transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of preferably from about 10 mg to about 10,000 mg, more preferably from about 20 mg to about 1,000 mg, should be appropriate, although the upper limit may be exceeded when indicated. The daily dosage can be administered as a single dose or in separate doses, or for parenteral administration, it may be given as continuous infusion.

The compounds of the present invention can be prepared according to the following procedure:

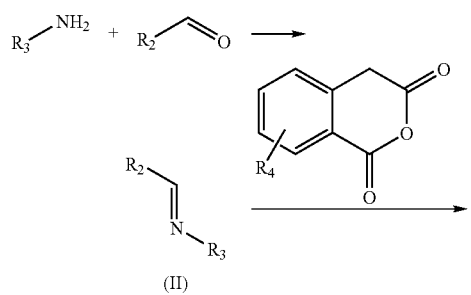

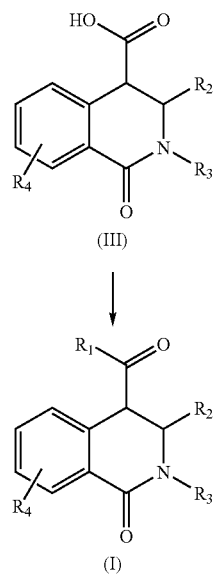

An amine and an aldehyde are reacted to give an azomethine of the formula II, this azomethine is reacted with an homophthalic acid anhydride, giving compounds of formula III, which are then converted to esters, amides or left unchanged to give compounds of formula I. These compounds of formula I can be further derivatized such as making esters or salts from acids, salts from amines or cleaving protecting groups found in substituents found in R1 to R4. Such methods are known for those skilled in the art (cf. e.g., J. S. Yadaf et al., Tetrahedron, 2003, 59, 1805-1809; L. Wang et al., Adv. Synth. Catal., 2005, 347, 689-694).

The present invention encompasses the following Examples.

Example 1

General Procedure

Equimolar amounts of an aldehyde and a primary amine are added at room temperature in a solvent like dichloromethane, tetrahydrofurane, chloroforme, methanol or ethanol to form the corresponding azomethine. A dehydrating agent like a mol sieve can be added to facilitate the reaction. After 1 day of reaction, equimolar amounts of a homophthalic acid anhydride derivative is added and refluxed. After 1 day of reaction the reaction mixture is cooled down. The resulting 1-oxo-1,2,3,4-tetrahydro-isoquinoline-4-carboxylic acid derivative is filtered off if it has precipitated out, or after removal of the solvent in vacuum, the product is re-crystallized from ethanol or purified via standard column chromatographic methods.

Example 2

According to the general procedure in example 1, the following compounds were prepared:
2.a 2-(4-Chloro-benzyl)-3-(4-chloro-phenyl)-1-oxo-1,2,3,4-tetrahydro-isoquinoline-4-carboxylic acid. Molecular Weight=426.3028, calculated from Molecular Formula=C23H17Cl2NO3. (M$^+$) observed 426.5.
2.b 2,3-Bis-(4-chloro-phenyl)-1-oxo-1,2,3,4-tetrahydro-isoquinoline-4-carboxylic acid. Molecular Weight=412.2758, calculated from Molecular Formula=C22H15Cl2NO3. (M$^+$) observed 412.3.

2.c 3-(4-Chloro-benzyl)-2-(4-chloro-phenyl)-1-oxo-1,2,3,4-tetrahydro-isoquinoline-4-carboxylic acid. Molecular Weight=426.3028, calculated from Molecular Formula=C23H17Cl2NO3. (M$^+$) observed 426.3.

2.d 2-(4-Chloro-benzyl)-3-(1H-indol-3-yl)-1-oxo-1,2,3,4-tetrahydro-isoquinoline-4-carboxylic acid. Molecular Weight=430.8948, calculated from Molecular Formula=C25H19ClN2O3. (M$^+$) observed 431.0.

2.e 2-[Carboxy-(4-chloro-phenyl)-methyl]-3-(4-chloro-phenyl)-1-oxo-1,2,3,4-tetrahydro-isoquinoline-4-carboxylic acid. Molecular Weight=470.3128, calculated from Molecular Formula=C24H17Cl2NO5. (M$^+$) observed 470.1.

2.f 2-(4-Chloro-benzyl)-1-oxo-3-quinolin-3-yl-1,2,3,4-tetrahydro-isoquinoline-4-carboxylic acid. Molecular Weight=442.9059, calculated from Molecular Formula=C26H19ClN2O3. (M$^+$) observed 443.0.

Example 3

General Procedure

Compounds prepared according to the general procedure in example 1 are dissolved in dimethylformamide and amine were coupled using standard peptide coupling conditions. Thus, for example the coupling agent EDCI is added to the solution of the acid in DMF, reacted for 30 minutes and then the corresponding amine is added and allowed to react for 2 days at room temperature. Ethylacetate and water is then added to the reaction mixture, the organic layer is separated and washed several times with water. After removing the ethylacetate, the final product is purified either by re-crystallization from ethanol or by standard column chromatographic methods. Using this procedure, the following compounds were prepared:

3.a 2-(4-Chloro-benzyl)-3-(4-chloro-phenyl)-1-oxo-1,2,3,4-tetrahydro-isoquinoline-4-carboxylic acid (2-methoxy-ethyl)-amide. Molecular Weight=483.3988, calculated from Molecular Formula=C26H24Cl2N2O3. ([M+H]$^+$) observed 463.4.

3.b 2,3-Bis-(4-chloro-phenyl)-1-oxo-1,2,3,4-tetrahydro-isoquinoline-4-carboxylic acid 2-methoxyethyl-amide. Molecular Weight=469.3717, calculated from Molecular Formula=C25H22Cl2N2O3. ([M+H]$^+$) observed 469.2.

3.c 3-(4-Chloro-benzyl)-2-(4-chloro-phenyl)-1-oxo-1,2,3,4-tetrahydro-isoquinoline-4-carboxylic acid (2-methoxy-ethyl)-amide. Molecular Weight=483.3988, calculated from Molecular Formula=C26H24Cl2N2O3. ([M+H]$^+$) observed 482.1.

3.d 2-(4-Chloro-benzyl)-3-(1H-indol-3-yl)-1-oxo-1,2,3,4-tetrahydro-isoquinoline-4-carboxylic acid (2-methoxy-ethyl)-amide. Molecular Weight=487.9907, calculated from Molecular Formula=C28H26ClN3O3. ([M+H]$^+$) observed 488.0.

3.e 2-(4-Chloro-benzyl)-1-oxo-3-quinolin-3-yl-1,2,3,4-tetrahydro-isoquinoline-4-carboxylic acid (2-methoxyethyl)-amide. Molecular Weight=500.0019, calculated from Molecular Formula=C29H26ClN3O3. ([M+H]$^+$) observed 500.1.

3.f 2-(4-Chloro-benzyl)-3-naphthalen-2-yl-1-oxo-1,2,3,4-tetrahydro-isoquinoline-4-carboxylic acid (2-methoxy-ethyl)-amide. Molecular Weight=499.0143, calculated from Molecular Formula=C30H27ClN2O3. ([M+H]$^+$) observed 498.8.

3.g 2-(4-Chloro-benzyl)-3-(4-chloro-phenyl)-4-(morpholine-4-carbonyl)-3,4-dihydro-2H-isoquinolin-1-one; Molecular Weight=495.4099, calculated from Molecular Formula=C27H4Cl2N2O3. (M$^+$) observed 495.4.

3.h 4-(4-Acetyl-piperazine-1-carbonyl)-2-(4-chloro-benzyl)-3-(4-chloro-phenyl)-3,4-dihydro-2H-isoquinolin-1-one; Molecular Weight=536.4628, calculated from Molecular Formula=C29H27Cl2N3O3. (M$^+$) observed 536.6.

3.i 4-(4-Acetyl-piperazine-1-carbonyl)-2-(4-chloro-benzyl)-3-(4-chloro-phenyl)-3,4-dihydro-2H-isoquinolin-1-one; Molecular Weight=536.4628, calculated from Molecular Formula=C29H27Cl2N3O3. (M$^+$) observed 536.6.

3.j 2-(4-Chloro-benzyl)-3-(4-chloro-phenyl)-1-oxo-1,2,3,4-tetrahydro-isoquinoline-4-carboxylic acid (2-hydroxy-ethyl)-amide; Molecular Weight=469.3717, calculated from Molecular Formula=C25H22Cl2N2O3. (M$^+$) observed 469.5.

3.k 2-(4-Chloro-benzyl)-3-(4-chloro-phenyl)-4-[4-(2-hydroxy-ethyl)-piperazine-1-carbonyl]-3,4-dihydro-2H-isoquinolin-1-one; Molecular Weight=538.4788, calculated from Molecular Formula=C29H29Cl2N3O3. (M$^+$) observed 538.5.

Example 4

Using 4-chlorophenyl-2-amino-acetic acid methyl ester as a primary amine, (4-Chloro-phenyl)-[3-(4-chloro-phenyl)-4-(2-methoxy-ethylcarbamoyl)-1-oxo-3,4-dihydro-1H-isoquinolin-2-yl]-acetic acid methyl ester was prepared according to the general procedure of example 1 and 3. The final acid (4-Chloro-phenyl)-[3-(4-chloro-phenyl)-4-(2-methoxy-ethylcarbamoyl)-1-oxo-3,4-dihydro-1H-isoquinolin-2-yl]-acetic acid was prepared by treatment with lithium hydroxide in tetrahydrofuran. Molecular Weight=527.4087, calculated from Molecular Formula=C27H24Cl2N2O5. ([M+H]$^+$) observed 526.9.

Example 5

In Vitro Activity Cell-Free Assay

The ability of the compounds to bind to HDM2 and to inhibit the interaction between HDM2 and proteins that are p53-like was judged by using an ELISA (Enzyme-Linked Immuno Sorbent Assay). Test plates were prepared by coating with streptavidin followed by a PBS (phosphate-buffered saline) wash and overnight blocking with a buffer containing bovine serum albumin (BSA) in a PBS buffer. N-terminal biotinylated peptide Ser-Gln-Glu-Thr-Phe-Ser-Asp-Leu-Trp-Lys-Leu, a peptide that is homologous to the HDM2-interacting region of p53 (Blommers et al. J. Am. Chem. Soc. 1997, 119, 3425-3426) is added to each well in blocking buffer and washed after incubation. Test compounds were incubated with a mix of the HDM2 protein and an anti-HDM2 antibody (SMP-14, Santa Cruz Biotech) in a separate plate. After incubation, the content of the plate is transferred and incubated in the test plate. The secondary anti-mouse IgG antibody (peroxydase linked anti-mouse IgG, Roche Molecular Biochemicals) is added to the test plate preceded and followed by a wash with 0.05% Tween 20 in PBS. Finally, peroxydase substrate (MTB Microwell Peroxydase Substrate System, Kirkegaard & Perry Labs) is added to each well and the absorption was read at 450 nm. The inhibitory activity of the test compounds was measured as a percentage of the bound HDM2 in treated vs. untreated wells and IC50 was calculated.

Example 6

In Vitro Activity Cell-Free Assay

The ELISA plates (MaxiSorp-Nunc) were coated with GST-HDM2 protein or GST protein diluted in PBS as a control. After washing with a solution containing PBS, the plates were incubated with blocking solution containing BSA/mL and washed. A solution of the compounds to be tested on p53 protein was incubated. After an additional washing, the plates were incubated with the monoclonal antibody Pab42123 (Oncogene Science) in a blocking solution.

The plates were washed and incubated with a goat antimouse IgG antibody coupled to alkaline phosphatase (Promega) diluted in blocking solution. The excess of antibody was removed with washing solution, and the coupled antibody was detected with a solution of p-nitrophenyl phosphate salt. The absorbance was measured at 405 nm.

The invention claimed is:

1. A compound of formula I and a pharmaceutically acceptable salt or ester thereof,

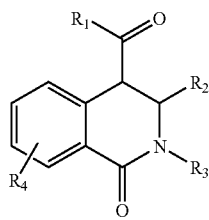

formula I wherein R1 is selected from substituted or unsubstituted morpholinyl, substituted or unsubstituted pyrrolidinyl and substituted or unsubstituted piperazinyl or —NX1(X2), with X1 and X2 independently selected from H, alkyl, cycloalkyl, heteroalkyl, aryl, heteroaryl, arylalkyl or heteroarylalkyl, wherein R2 and R3 are each independently selected from 3- or 4-halogen substituted phenyl or benzyl, wherein R4 is selected from —H, —F, —Cl, —Br, —I, —NO2, hydroxy, lower alkyl, lower alkenyl or lower alkynyl, lower alkoxy, lower alkoxy alkyl —NY1(Y2), with Y1 and Y2 independently selected from H, lower alkyl, lower alkoxy alkyl, heteroalkyl, aryl or heteroaryl.

2. A compound of formula I and a pharmaceutically acceptable salt or ester thereof,

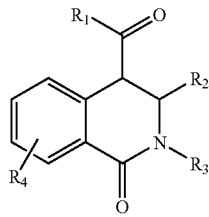

formula I wherein R1 is —NX1(X2), with X1 and X2 independently selected from H, alkyl, cycloalkyl, heteroalkyl, aryl, heteroaryl, arylalkyl or heteroarylalkyl, wherein R2 and R3 are each independently selected from 3- or 4-halogen substituted phenyl or benzyl, wherein R4 is selected from —H, —F, —Cl, —Br, —I, —NO2, hydroxy, lower alkyl, lower alkenyl or lower alkynyl, lower alkoxy, alkoxyalkyl, —NY1(Y2), with Y1 and Y2 independently selected from H, lower alkyl, lower alkoxy alkyl, heteroalkyl, aryl or heteroaryl.

3. A compound according to claim 2, wherein R2 is selected from 3- or 4-fluorophenyl, 3- or 4-chlorophenyl, 3- or 4-bromophenyl, 3- or 4-iodophenyl and R3 is selected from 3- or 4-fluorobenzyl, 3- or 4-chlorobenzyl, 3- or 4-bromobenzyl, 3- or 4-iodobenzyl.

4. A compound according to claim 2, wherein R1 is selected from N-2-hydroxyethyl-piperazinyl, 2-oxo-N-alkyl-piperazinyl, 2-oxo-N-heteroalkyl-piperazinyl.

5. A compound according to claim 2, wherein R1 is —NH(X2), wherein X1 is selected from —H or lower alkyl, and X2 is selected from H, —CH2CH2OH, —CH2CH2OCH3, lower alkyl, lower heteroalkyl, cycloalkyl, heteroalkyl, aryl, heteroarylalkyl, arylalkyl or heteroarylalkyl.

6. A compound according to claim 2, selected from the group of: 2-(4-Chloro-benzyl)-3-(4-chloro-phenyl)-1-oxo-1,2,3,4-tetrahydro-isoquinoline-4-carboxylic acid (2-methoxymethyl)-amide; 2,3-Bis-(4-chloro-phenyl)-1-oxo-1,2,3,4-tetrahydro-isoquinoline-4-carboxylic acid methoxymethyl-amide; 3-(4-Chloro-benzyl)-2-(4-chloro-phenyl)-1-oxo-1,2,3,4-tetrahydro-isoquinoline-4-carboxylic acid (2-methoxymethyl)-amide; (4-Chloro-phenyl)-[3-(4-chloro-phenyl)-4-(methoxymethyl-carbamoyl)-1-oxo-3,4-dihydro-1H-isoquinolin-2-yl]-acetic acid; 2-(4-Chloro-benzyl)-3-(4-chloro-phenyl)-4-(morpholine-4-carbonyl)-3,4-dihydro-2H-isoquinolin-1-one; 4-(4-Acetyl-piperazine-1-carbonyl)-2-(4-chloro-benzyl)-3-(4-chloro-phenyl)-3,4-dihydro-2H-isoquinolin-1-one; 4-(4-Acetyl-piperazine-1-carbonyl)-2-(4-chloro-benzyl)-3-(4-chloro-phenyl)-3,4-dihydro-2H-isoquinolin-1-one; 2-(4-Chloro-benzyl)-3-(4-chloro-phenyl)-1-oxo-1,2,3,4-tetrahydro-isoquinoline-4-carboxylic acid (2-hydroxy-ethyl)-amide; 2-(4-Chloro-benzyl)-3-(4-chloro-phenyl)-4-[4-(2-hydroxy-ethyl)-piperazine-1-carbonyl]-3,4-dihydro-2H-isoquinolin-1-one.

* * * * *